United States Patent [19]

Kirchanski et al.

[11] Patent Number: 4,581,334
[45] Date of Patent: Apr. 8, 1986

[54] SIMULTANEOUS DETECTION OF LEUKOCYTE PHAGOCYTIC AND KILLING ABILITY

[75] Inventors: Stefan J. Kirchanski, Framingham; Giora Davidovits, Brookline; Robert A. Hoffman, Mansfield, all of Mass.

[73] Assignee: Ortho Diagnostics Systems, Inc., Raritan, N.J.

[21] Appl. No.: 487,944

[22] Filed: Apr. 25, 1983

[51] Int. Cl.$^4$ .................. G01N 33/48; G01N 33/49
[52] U.S. Cl. ................... 435/29; 250/461.2; 356/39; 436/63; 436/164; 436/172
[58] Field of Search ............. 436/63, 164, 172, 519, 436/807; 422/52, 68; 250/461.2; 356/39; 435/29

[56] References Cited

U.S. PATENT DOCUMENTS

| | | | |
|---|---|---|---|
| 3,883,247 | 5/1975 | Adams | 250/461.2 X |
| 3,916,205 | 10/1975 | Kleinerman | 250/461.2 |
| 4,243,318 | 1/1981 | Stohr | 250/461.2 X |
| 4,336,029 | 6/1982 | Natale | 436/172 |

OTHER PUBLICATIONS

Hafeman, D. G. et al., "Specific Antibody-Dependent Interactions Between Macrophages and Lipid Haptens in Planar Lipid Monolayers", Proc. Natl. Acad. Sci., vol. 78, 7:4552-4556, Jul. 1981.
Glick, D., "Microchemical Analytical Techniques of Potential Clinical Interest", Clin. Chem. 23/8, 1465-1471 (1977).
Hafeman, D. G., et al., "Neutrophil Activation Monitored by Flow Cytometry: Stimulation by Phorbol Diester is an All-or-None Event", Science, 215:673-675, (2/5/82).
Hultborn, R., et al., "Studies on Leucocyte Function by Measuring Respiration and Nitroblue Tetrazolium Reduction by Simplified Methods", Scand. J. Clin. Lab. Invest., 23, 297 (1973).

*Primary Examiner*—Sidney Marantz
*Attorney, Agent, or Firm*—Audley A. Ciamporcero, Jr.; Mark A. Hofer

[57] ABSTRACT

Methods for the determination of phagocytic and killing ability of selected leukocyte subclasses based upon the use of three part differentials obtained by light scatter characteristics and gated fluorescence. Particles having multiple fluorescent labels associated therewith, one of which is sensitive to reactive oxygen, incubated with the leukocytes. Detection of the fluorescent labels permits identification of cells having phagocytic ability, as determined by presence of the non-sensitive label, and also the identification of those with killing ability as determined by the decrease in fluorescence from the sensitive label.

13 Claims, 16 Drawing Figures

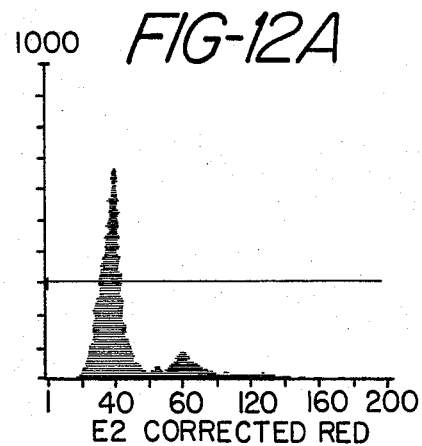
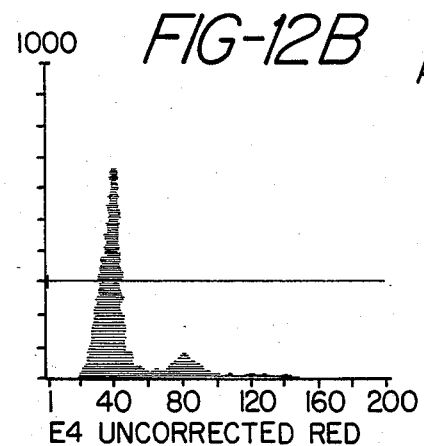
| HIST | LC | UC | COUNT | %TOT | PEAK | MEAN | SD | CY | CY(HM) |
|---|---|---|---|---|---|---|---|---|---|
| E4 | 1 | 200 | 13921 | 100.0 | 1.0 | 43.8 | 26.5 | 60.6 | .0 |
| E2 | 1 | 200 | 13921 | 100.0 | 1.0 | 43.7 | 26.5 | 60.6 | .0 |
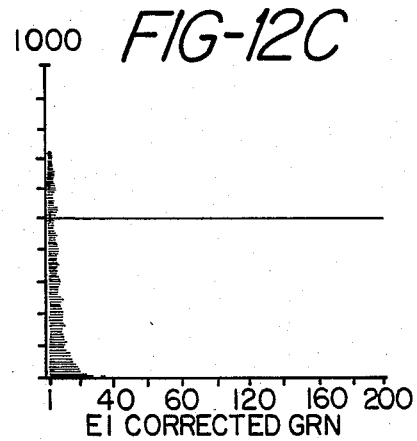
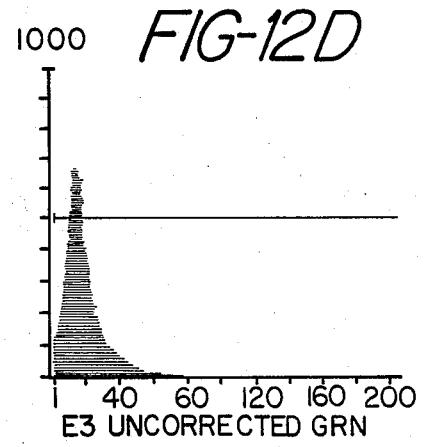
E3 IS GREEN SPILL OVER OF RED PARTICLES
E1 IS CORRECTED GREEN FOR THE SPILLOVER
| HIST | LC | UC | COUNT | %TOT | PEAK | MEAN | SD | CY | CY(HM) |
|---|---|---|---|---|---|---|---|---|---|
| E3 | 1 | 200 | 13921 | 100.0 | 1.0 | 18.7 | 13.8 | 73.5 | .0 |
| E1 | 1 | 200 | 13921 | 100.0 | 1.0 | 3.0 | 4.8 | 157.9 | .0 |

FIG-13

PHAGOCYTOSIS AND C3b RECEPTORS

| INCUBATION | GREEN | SET1 1 | 2 | 3 | 4 | % | # | RED | SET2 | SET3 |
|---|---|---|---|---|---|---|---|---|---|---|
| 3 MIN | 38.0<br>38.0<br>38.9 | 46.9 | 43.3 | 64.9 | 38.0 | 4.8<br>3.8<br>1.8 | 237<br>184<br>100 | 42.5 | 22.1 | 48.0 |
| 5 MIN | 59.2<br>59.2<br>60.3 | 66.3 | 63.8 | 78.3 | 59.2 | 9.1<br>6.5<br>2.8 | 495<br>342<br>161 | 43.4 | 16.4 | 47.8 |
| 10 MIN | 75.2<br>75.4<br>76.4 | 74.0 | 74.3 | 80.5 | 76.3 | 18.4<br>13.4<br>5.4 | 954<br>670<br>307 | 43.5 | 26.0 | 50.3 |
| 15 MIN | 82.1<br>82.1<br>82.6 | 78.8 | 80.2 | 81.2 | 83.4 | 23.0<br>15.9<br>8.5 | 980<br>679<br>439 | 43.1 | 20.3 | 56.2 |
| 20 MIN | 80.2<br>80.1<br>81.6 | 79.2 | 77.5 | 83.1 | 82.2 | 24.8<br>16.3<br>10.8 | 1063<br>677<br>542 | 42.8 | 27.3 | 65.1 |
| 30 MIN | 72.9<br>73.2<br>74.7 | 70.1 | 67.3 | 74.0 | 77.4 | 30.4<br>19.4<br>13.9 | 905<br>547<br>488 | 43.5 | 23.7 | 51.2 |
| 40 MIN | 74.2<br>74.2<br>76.1 | 73.3 | 73.9 | 75.2 | 76.4 | 34.3<br>20.8<br>17.4 | 1492<br>877<br>909 | 43.4 | 25.2 | 59.8 |

SET 1 - PARTICLES & anti C3bR
SET 2 - PARTICLES & O
SET 3 - O & anti C3bR

GREEN ... mean corrected green of granulocyte region
1 ... mean corrected green of all phagocytosing cells
2 ... mean corrected green of cells ingesting one particle
3 ... mean corrected green of cells ingesting more than one particle
4 ... mean corrected green of cells ingesting no particles

SIMULTANEOUS DETECTION OF LEUKOCYTE PHAGOCYTIC AND KILLING ABILITY

BACKGROUND OF THE INVENTION

This invention relates to flow cytometric applications to be performed on blood cells and specifically relates to methods for determining the competence of leukocyte phagocytic and leukocyte killing ability by utilizing the methods of flow cytometry.

The monitoring of leukocyte function is becoming of increasing clinical importance, particularly with regard to the pathology of autoimmune and arthritic diseases. Other reasons for inquiry into leukocyte abilities pertain to the healing processes such as those encountered in burn patients. See for instance Ransjo et al., "Some Aspects of Neutrophil Granulocyte Function in Burn Patients", Burns, 5:255-259 (1979), printed in Great Britain and given at the Fifth International Congress on Burn Injuries, Stockholm, June 1978. Further reference may be made to an article by Halgren et al., "The Serum Independent Particle Uptake by PMN From Patients With Rheumatoid, Arthritis and Systemic Lupus Erythematosis", Arthritis and Rheumatism, 21:107-113 (1978) and to Hakansson, et al., "Neutrophil Function In Infection Prone Children", Archives of Disease in Childhood, 55:776-781, (1980).

The particular aspects of leukocyte function monitoring which are becoming of increasing clinical importance involve the cell's ability to phagocytose, i.e., the ability to ingest foreign particles, and the leukocyte's killing ability, i.e., the ability to destroy ingested organisms through the application of reactive oxygen. For further information, reference may be made to articles by Stossel et al., "Quantitative Studies of Phagocytosis by PMN Leukocytes: Use of Emulsions to Measure the Initial Rate of Phagocytosis", The Journal of Clinical Investigations, 51:615-624 (1972); Michell et al., "Measurement of Rates of Phagocytosis: The Use of Cellular Monolayers", J. Cell Biol. 40:216-224, 1969; and Arnaout et al., "Alternative Complement Pathway Dependent Ingestion of Fluolite Particles by Human Granulocytes", The J. of Immunology, 127:278-281 (1981).

Active oxygen is the species of oxygen used by phagocytic cells to kill foreign organisms generally by way of oxidative cytotoxic related mechanisms. It has been previously measured by monitoring neutrophil respiratory events for producing active oxygen and detecting the effects on autofluorescence. See: "Neutrophil Activation Monitored by Flow Cytometry: Stimulation by Phorbol Diester is an All-or-None Event", Science, Vol. 215:673-675 (Feb. 5, 1982). Still other microchemical techniques for the cellular spectrophotometric measurement of oxygen uptake have been described by Glick in an article entitled "Microchemical Analytical Techniques of Potential Clinical Interest", in Clinical Chemistry, Vol. 23, No. 8:1465-1471 (1977). Hultborn et al., described yet additional studies on oxygen consumption rate and nitroblue tetrazolium reduction capacity in the absence and presence of phagocytogenic agents. That article was reported in the Scandanavian Journal of Clinical Laboratory Investigations, 23, 297-304 (1973) in an article entitled, "Studies on Leukocyte Function by Measuring Respiration and Nitroblue Tetrazolium Reduction by Simplified Methods".

Other cellular activation and membrane effects have been described using solid monolayer membranes, fluorescent lipid probes and bound fluorescent antibodies in an article entitled, "Specific Antibody Dependent Interactions Between Macrophages and Lipid Haptens in Planar Lipid Monolayers", Proc. Natl. Acad. Sci., Vol. 78, No. 7:4552-4556 (July 1981). Still other references of general interest include Gordon, "Regulation of Hematopoiesis", Vol. 2, Chapter 42, 1970, Appleton - Century Crofts New York; and Halgren et al. "The Serum-Independent Uptake of IgG-Coated Particles by Polymorphonuclear Leukocytes From Uremic Patients on Regular Dialysis Treatment", J. Lab. Clin. Med. 94:277-284 (1979).

Despite an intense interest in the various phagocytic and killing ability characteristics of leukocytes, the conventional methods have failed to provide suitable methods for the convenient assay of both phagocytic and killing ability.

It is an object of the present invention to provide such methods in a convenient assay and to thereby enable one to efficiently measure both the phagocytic and killing ability of leukocytes. It is another object to allow such measurements to be made on selected leukocyte subclasses. It is a further object to provide such assays for use in flow cytometry type instruments thereby permitting the rapid evaluation of large numbers of cells in a clinically convenient environment and acceptable format.

It is yet another object of the present invention to provide methods capable of relating phagocytic ability of leukocytes with the presence or absence of specified cell surface markers or antigens.

SUMMARY OF THE INVENTION

These and other objectives of the present invention are met by the methods of the present invention which provide for assays permitting the determination of phagocytic ability of selected subclasses of leukocytes and the determinations of the cells respective killing abilities. The leukocytes to be measured, typically contained within a blood sample, are contacted with target particles having a first label associated therewith. In a preferred embodiment, this first label is a fluorescent label such as tetramethyl rhodamine. These same target particles may be preferably opsonized by having immunoglobulins coated thereon. The thusly treated leukocytes are thereafter passed in a substantially single file fashion pursuant to conventional and well-known hydrodynamic focusing techniques, through a zone illustrated by a focused light source. The passage of the cells through this zone results in a pattern of scattering characteristic of the respective leukocyte subclasses. Specifically, the scattered light is detected at substantially forward angle and wide angle locations and leukocytes identified accordingly. The relative wide angle scatter characteristics of different types of leukocytes are relatively insensitive to angles of measurement over at least the range 32° to 148°. Theoretical and experimental considerations [Hansen, et al. "Light Scatter as an Adjunct to Cellular Immunofluorescence in Flow Cytometric Systems", Journal of Clinical Immunology, 2:325-415 (1982)] indicate that scattering angles below 2° give primarily size information, while angles above 4° are dependent on granularity properties of the cell. Thus, the class of leukocytes (white blood cells) may be differentiated into monocytes, granulocytes and lymphocytes. These individual leukocyte subclasses may then be further individually examined by conventional electronic gating means and the fluorescence of the cells detected whereby the presence or absence of phagocytized fluorescent particles may be determined.

Other embodiments provide for the correlation of phagocytosing ability as determined above with additional cellular characteristics such as the presence or absence of particular surface antigens detectable by antibodies specific therefor. These antibodies are labeled with a second detectable label, preferably different from the first label. Most preferably, the second label will be a chromophore or other fluorescent type label having fluorescence different than that of the label employed in the target particle.

Still additional methods provide for the determination of killing ability to the extent it is related to the production of reactive oxygen. The presence of reactive oxygen is detected by the change in the ratio of an oxidatively sensitive fluorophore against a nonoxidatively sensitive fluorophore, both of which are associated with a target particle ingested by the leukocyte.

BRIEF DESCRIPTION OF THE DRAWINGS

These and other principles of the instant invention may be more clearly understood by reference to the figures wherein:

FIG. 12a shows a histogram of the corrected red fluorescent particles in a correlation study between phagocytosis and C3b receptors;

FIG. 12b is a histogram of the uncorrected red fluorescent particles in a correlation study between phagocytosis and C3B receptors;

FIG. 12c is a histogram of the corrected green fluorescence;

FIG. 12d is a histogram of uncorrected green fluorescence; and

FIG. 13 graphically depicts a time related correlation study between phagocytosis and C3b receptors.

DETAILED DESCRIPTION OF THE DRAWINGS AND PREFERRED EMBODIMENTS

Whole blood samples may be analyzed and the leukocytes or white blood cells therein separated into a three part differential by means of the cells' light scatter characteristics. Particularly useful in such an analysis is the forward light scatter and right angle light scatter measurement such as those made by the Spectrum III ™ flow cytometry instrument available from Ortho Diagnostic Systems Inc., Raritan, N.J. The experimenter typically lyses the red blood cells in a whole blood sample, stains and dilutes the sample appropriately, and in a process conventionally known as hydrodynamic focusing, forms a substantially one cell wide column of cells surrounded by a sheath fluid. This stream is passed through a zone illuminated by a focused light source. Such a light source may preferably be a laser, the spectral characteristics of which may be advantageously selected in accordance with the fluorescent dyes employed.

Figure 1:
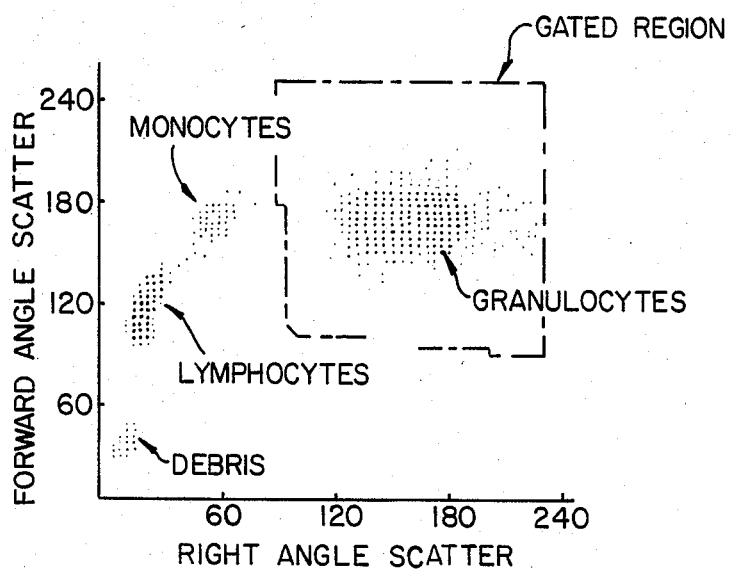
FIG. 1 depicts a conventional gating analysis on the well-known three part differential.
Figure 2:
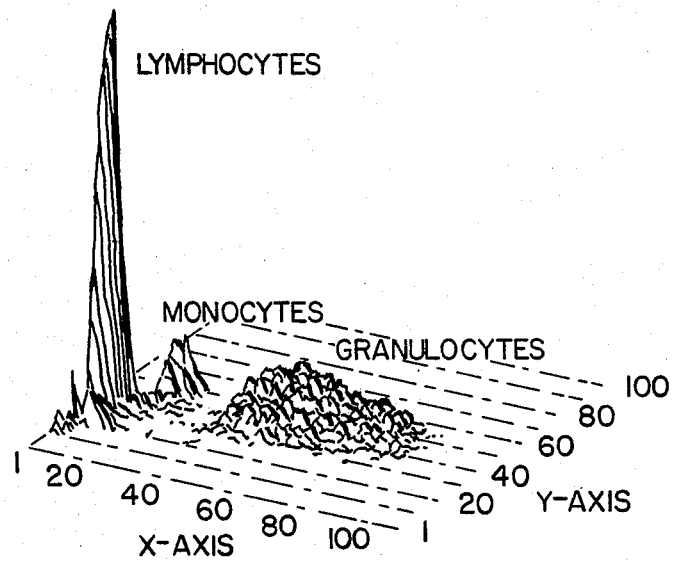
FIG. 2 depicts the same analysis in a three dimensional view.

As the cells pass through the aforementioned zone, the light is scattered in a manner characteristic of cellular subclasses. As is now well-known, comparison of forward angle light scatter against right angle light scatter, permits the leukocytes to be differentiated into the respective categories of lymphocytes, monocytes and granulocytes. The resulting categories generally form clusters when the data is presented in a histogram format. Such a cluster arrangement is depicted in FIG. 1 and the respective clusters labeled. As is further shown in FIG. 1 and in a manner well-known in conventional art, a particular subclass such as the granulocytes may be gated as indicated by the dotted line region circumscribing the granulocyte cluster. This gating is typically accomplished by electronic means and is fully operator adjustable. FIG. 2 indicates an alternative manner of presenting the three part differential, whereby the Z axis or height is indicative of the numbers of cells detected.

The gated granulocyte cluster indicated in FIG. 1 may then be further analyzed with regard to one or two color fluorescence. Fluorescence is typically detected by utilizing a photomultiplier type detector means and spectral filters in manners well-known in the art. The leukocytes depicted in FIG. 1 were incubated with fluorescently labeled target particles and phagocytosis permitted to occur. The granulocyte cluster was then arbitrarily chosen for further analysis and a trigger region or gate constructed to surround these cells. Those cells included within the trigger region were then analyzed for green fluorescence indicative of the presence of ingested particles labeled with a green fluorescent chromophore. Those skilled in the art will readily recognize that fluorescent labels of other colors may be readily employed in substitution for the fluorescein used in this example and indeed, other types of labels such as colloidal gold and the like may be employed providing the labels have detectable effects preferably with respect to light.

Figure 3:
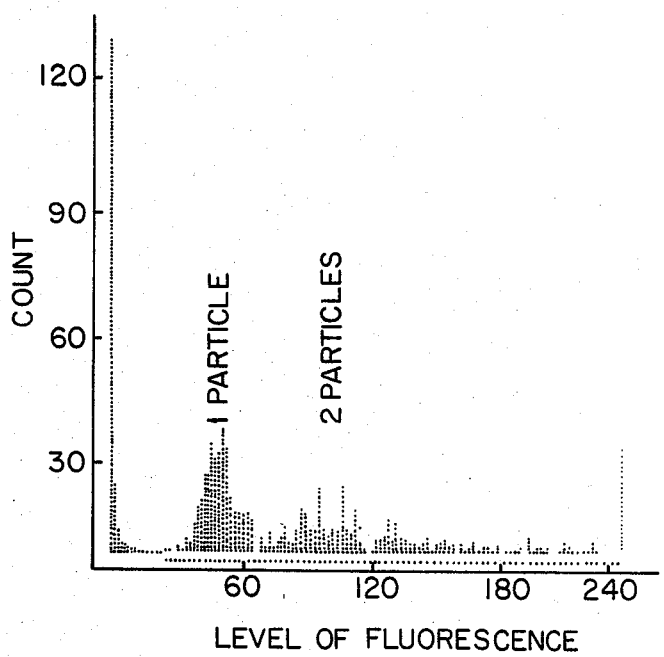
FIG. 3 depicts a fluorescence histogram analysis of granulocyte phagocytosis of fluorescent particles.

FIG. 3 presents a histogram relating the level of green fluorescence detected against the count or number of cells exhibiting fluorescence. As may be clearly determined by analysis of FIG. 3, the granulocytes may be further differentiated into subpopulations based on the number of fluorescent particles ingested. Those cells having a lower level of fluorescence correspond to cells having a single particle ingested while those cells exhibiting greater levels of fluorescence correspond to cells having additional particles ingested.

Figure 4:
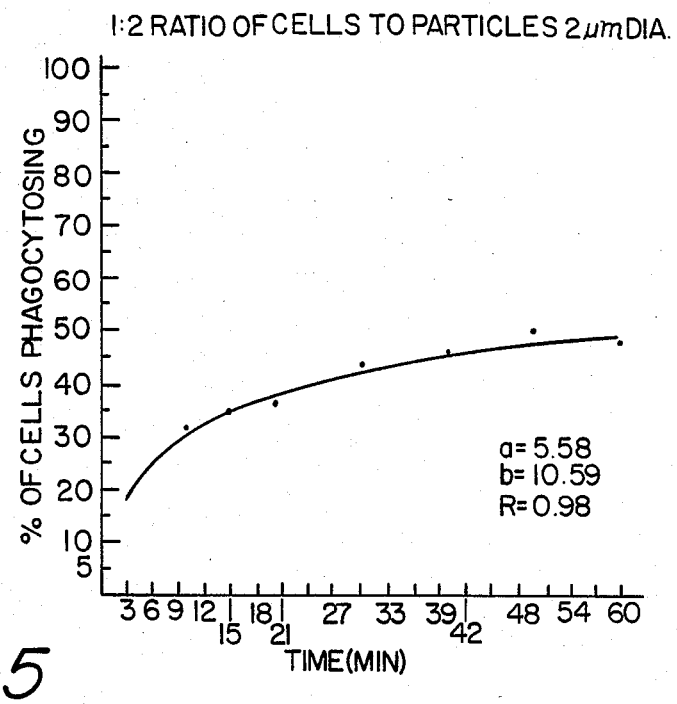
FIG. 4 shows a phagocytosis analysis based on a one to two ratio of cells to target particles.
Figure 5:
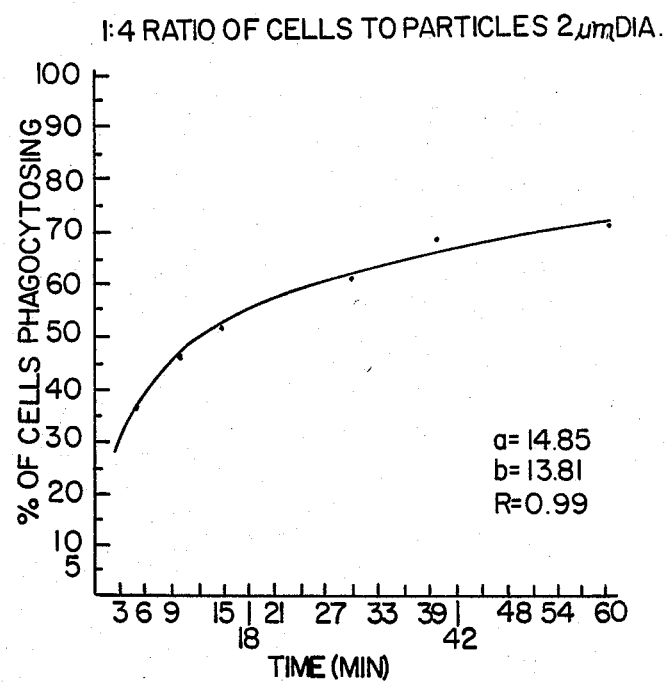
FIG. 5 shows a phagocytosis analysis based on a one to four ratio of cells to target particles.
Figure 6:
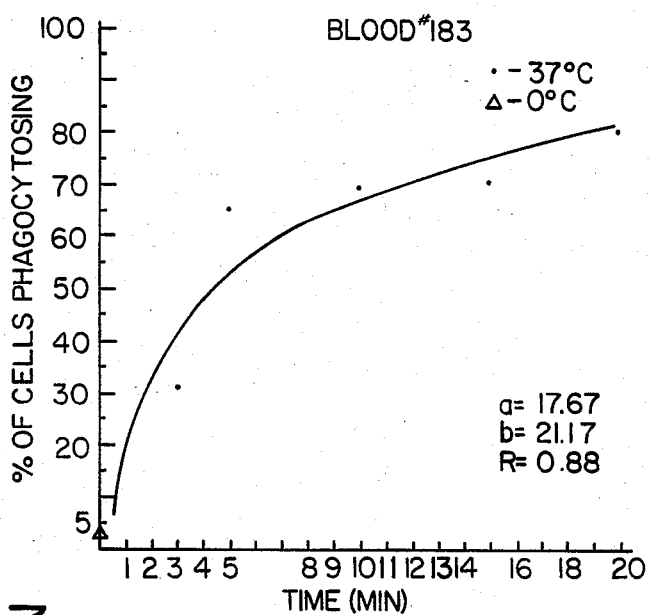
FIG. 6 depicts graphically a phagocytosis analysis on blood sample No. 183.
Figure 7:
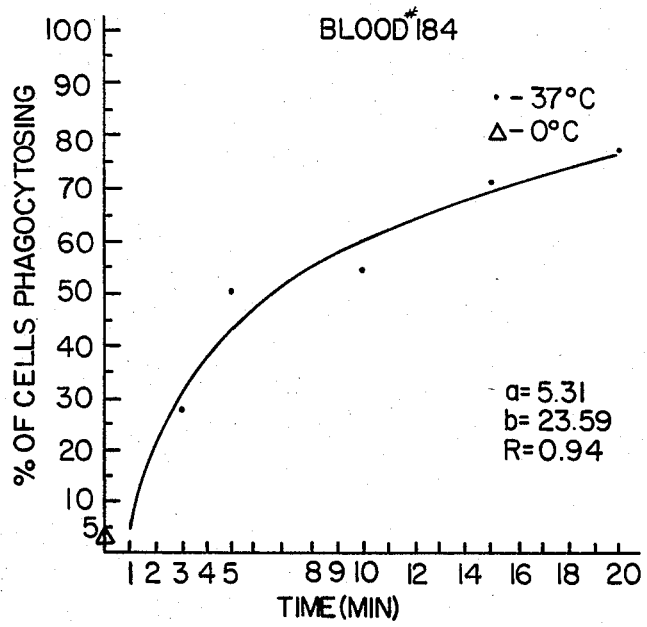
FIG. 7 depicts graphically a phagocytosis analysis on blood sample No. 184.
Figure 8:
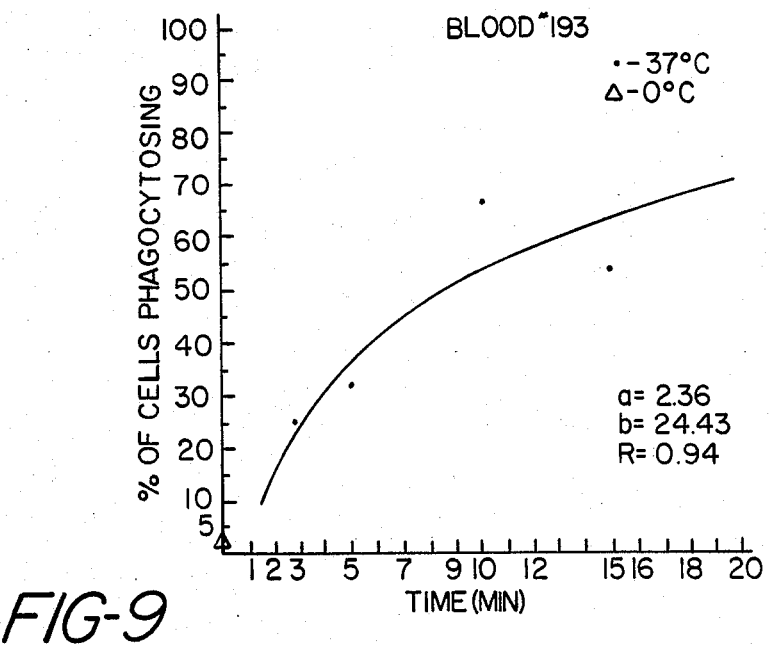
FIG. 8 depicts graphically a phagocytosis analysis on blood sample No. 193.
Figure 9:
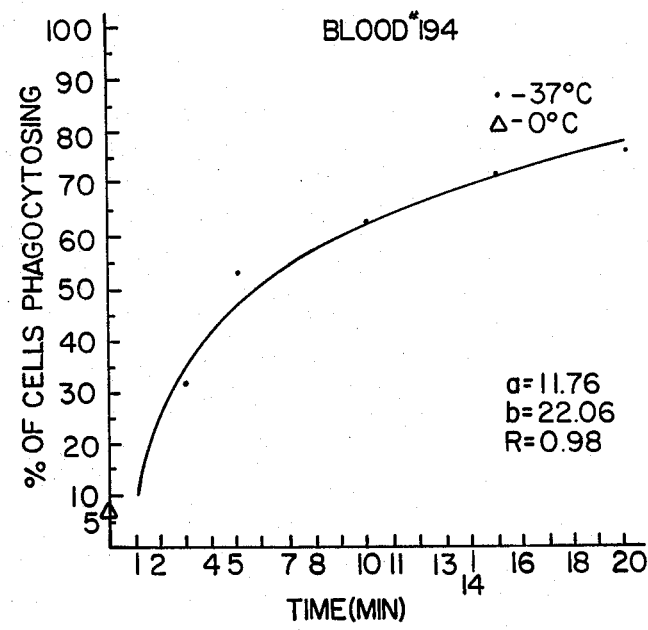
FIG. 9 depicts graphically a phagocytosis analysis on blood sample No. 194.
Figure 10:
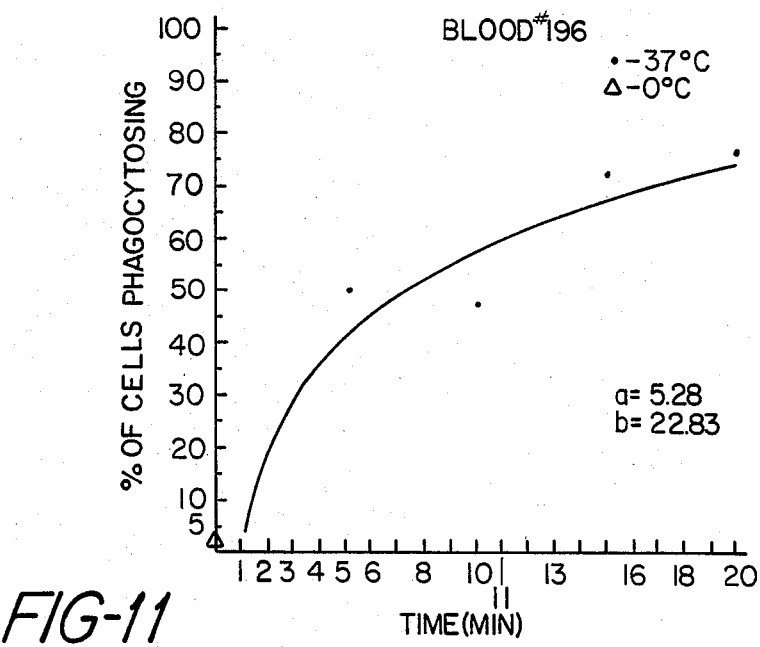
FIG. 10 depicts graphically a phagocytosis analysis on blood sample No. 196.
Figure 11:
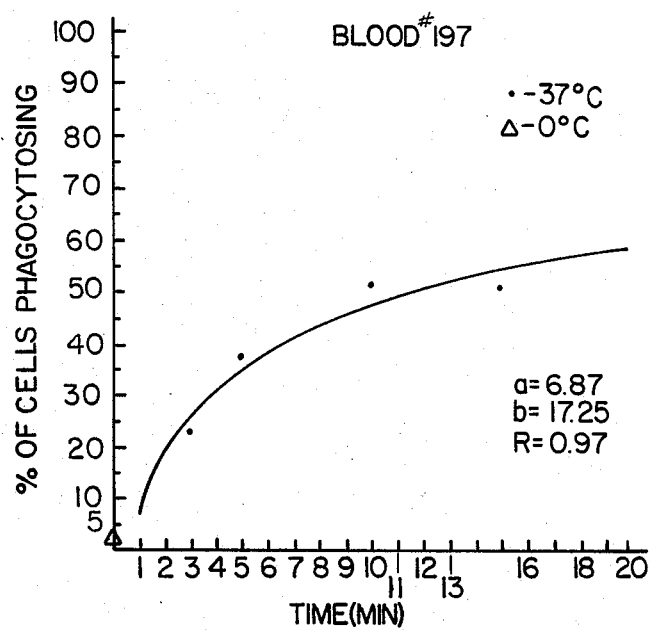
FIG. 11 depicts graphically a phagocytosis analysis on blood sample No. 197.

As may be readily appreciated, the number of particles ingested is at least partly related to the number of particles provided per number of cells capable of phagocytosing the particles. Thus, particle concentration can become a rate limiting factor. FIGS. 4 and 5 clearly depict this relationship and show the increase of percentage of cells phagocytosing identified when the ratio of cells to particles is altered from one to two (FIG. 4) to one to four (FIG. 5). The particles employed in both determinations were particles having a diameter of approximately two micrometers.

By performing a regression analysis on plotted curves of percents of cells phagocytosing over time, one may calculate an exponential fit relating the number of phagocytosing cells to time pursuant to the equation $$Y = a + b\, Ln(X)$$

where Y equals the percent of cells actively phagocytosing, X is the unit of time permitted for phagocytosis measured in minutes, a equals the Y intercept and b equals the slope. The constants and the standard deviations for FIGS. 4 and 5 have been calculated pursuant to such a regression analysis and are depicted thereon. Indeed, FIGS. 6 through 11 represent curves and calculated values resulting from like analysis of six different blood samples and clearly show the close correlation of uptake as a natural log function of time.

The target particles employed in the above experiments were fluorescent, monodispersed carboxylated microspheres in the one to two micrometer diameter range such as those obtainable from Polysciences under Catalog No. 15702. It should be noted, however, that although such a microsphere or bead represents the preferred target particle embodiment, other target particles may be employed such as bacteria and the like.

The Carboxylated Microspheres

Example 1—Method for Determining Phagocytic Ability

Fluorescent monodispersed carboxylated microspheres obtained from Polysciences, P.A. (No. 15702) diluted in glucose medium comprising:
Sodium Chloride—5.9 grams
Anhydrous Socium Acetate—2.5 grams
Potassium Chloride—0.3 grams
Calcium Chloride—0.44 grams
Magnesium Chloride—0.20 grams
Glucose—1.26 grams
(All quantities to 1 liter)
were opsonized by coating the particles with human IgG. 50 mg of human IgG and $2 \times 10^9$ particles were added to 10ml of 0.1M sodium borate-boric acid buffer, pH 8.2, and incubated for 48 hours at 4° C. with a constant stirring. The particles were then washed with a glucose suspension medium and suspended to the desired concentration.

The sample was prepared in the following manner: to 200 μl of blood, 200 μl of particles in the glucose medium were added and the resultant mixture incubated at 37° C. with gentle shaking. An identical sample was incubated at 0° C. to serve as a control. 100 μl of the incubated sample was lysed for five minutes with 2 ml of ammonium chloride based Ortho lysing reagent (available from Ortho Diagnostic Systems Inc., Raritan, N.J.) and analyzed on the Spectrum III TM flow cytometer (also available from Ortho Diagnostic Systems Inc.). The Spectrum III TM was configured to produce a forward versus right angle scatter three part differential with gated fluorescence.

It was surprisingly discovered that by employing multiple fluorescent colors, one may, in addition to determining phagocytic ability of a selected class of leukocytes, further determine the "killing ability" of the same cells. Such killing ability has typically been associated with the generation of so-called "reactive oxygen".

It has been theoretically proposed that reactive oxygen "kills" by oxidizing the phagocytosed particle, however, the exact mechanisms are still unknown.

By associating two labels with the target particle to be phagocytosed, one of which is photogenically sensitive to the presence of reactive oxygen, one may determine "killing ability" of the cell in question. The nonoxygen sensitive label, which may be chemically insensitive to active oxygen or protected from active oxygen, e.g., by being embedded in a plastic matrix, is utilized to indicate the presence or absence of the target particle within the cell. By measuring the two labels and determining the ratio therebetween, analysis of the killing ability may be effected without necessitating the measurement against controls. An example of the present invention employs fluorescent labels, the first label being tetramethyl rhodamine incorporated within the plastic bead while the surface of the bead or particle is labeled with fluorescein (green fluorescence as opposed to the rhodamine's red fluorescence), which is sensitive to the presence of the active oxygen. The combination of reactive oxygen with the fluorescein effectively causes photodecomposition of the fluorescein thereby resulting in high red/green fluorescent ratios. Cells exhibiting low red/green ratios, close to those exhibited by the particles themselves, indicate the presence of little or no reactive oxygen production. A preferred embodiment of the present invention would use a dye, such as a cyanine [di-O-C2-(3)], sensitive to active oxygen but not to the pH of the cell interior. Fluorescein is sensitive to pH as well as active oxygen.

The principles of the instant invention provide for still greater versatility and specifically allow for the correlation of phagocytosis with cellular surface markers of interest. An example of such a marker is the C3b receptor, the presence or absence of which is becoming increasingly important in the clinical environment. A correlation may be determined by the aforedescribed three part differential in conjunction with multiple gated fluorescence. For instance, red fluorescent particles are ingested by cells which are additionally incubated with fluorescein conjugated antibodies specific for the surface marker of interest such as the C3b receptor. As described earlier, the leukocyte subclass is indentified on the basis of its light scatter characteristics, the subclass of interest is gated and fluorescence measured. In the preferred embodiment, the particles are labeled with a rhodamine dye whereby the detection of red fluorescence serves as indication of phagocytic activity. The cells may be further interrogated for the presence of second fluorescent label (for instance the presence of fluorescein conjugated anti-C3b antibody) which presence is indicative of the C3b or other receptor on the cell surface.

With multiple fluorescence determinations, however, corrections may be necessary in the event of spectral overlap by fluorescence, for instance, between green fluorescence of the antibody and red fluorescence of the particle. Such a correction may be easily accomplished by treating three sets of samples in parallel wherein set 1 represents cells incubated with particles and anti-C3b; set 2 with particles and no anti-C3b; and set 3 no particles and only anti-C3b immunoglobulin. The following formulae were used:

$$\text{Green}_c = \text{Green}_m - \frac{\text{Green}_{mR}}{\text{Red}_{mR}} (\text{Red}_m)$$

$$\text{Red}_c = \text{Red}_m - \frac{\text{Red}_{mG}}{\text{Green}_{mG}} (\text{Green}_m)$$

(Where c=Corrected, m=Measured, G and R refer to measurement made with calibrating samples with only the green or red fluorochome respectively).

These corrections may be performed on a cell by cell basis by employing the Ortho 2150 computer in the list mode. FIGS. 12a through 12d indicate corrected red, uncorrected red, corrected green, and uncorrected green fluorescence respectively with the associated histogram counts.

FIG. 13 presents in tabular format an experiment preferred with three such sets of samples, incubated from 3-40 minutes and the resultant data therefor.

As may be readily appreciated by those skilled in the art, the above disclosure and figures demonstrate the principles and preferred embodiment of the instant invention, however, many alternatives are available, for instance the coating of a particle may be accomplished by absorption or by covalent linkage employing surface carboxyl groups on the particle etc. as well as other substitutions and variations on the described processes without deviating from the spirit or scope of the present invention.

What is claimed is:

1. A method for determining the phagocytic killing ability of cells comprising:
    (a) providing a sample containing the cells whose phagocytic killing ability is to be measured;
    (b) further providing target particles to be phagocytosed by said cells, said particles having associated therewith a first fluorescent label and a second fluorescent label having an emission spectrum substantially different from said first fluorescent label, said second fluorescent label also having a substantially greater photodecomposition sensitivity to reactive oxygen than said first fluorescent label;
    (c) adding said target particles to said blood sample under conditions surplusage to permit phagocytosis;
    (d) identifying the cells whose phagocytic killing ability is to be measured on the basis of light scatter characteristics;
    (e) detecting, from said identified cells, fluorescence from said first fluorescent label whereby the proportion of phagocytically competent cells may be determined; and
    (f) forming a ratio of the first fluorescence to the second fluorescence of said phagocytically competent cells whereby the killing ability of said cells may be determined, those with high ratios having greater killing ability than those with lower ratios.

2. The method as provided in claim 1 wherein the target particles are opsonized by having immunoglobulin coated thereon.

3. The method as provided in claim 2 wherein the target particles are selected from the group consisting of plastic beads having a diameter in the range of about one to two micrometers and bacteria.

4. The method as provided in claim 1 wherein the first fluorescent label is tetramethyl rohodamine and the second fluorescent label is fluorescein.

5. The method as provided in claim 4 wherein the target particles are selected from the group consisting of plastic beads having a diameter in the range of about one to two micrometers and bacteria.

6. The method of claim 1 wherein the cells are leukocytes which are provided in a blood sample and further comprising the steps of:
    (a) lysing substantially all erythrocytes contained within said blood sample; and
    (b) the identifying step comprises:
        (i) passing the leukocytes in substantially single file past a focused light source;
        (ii) detecting light scattered by said cells;
        (iii) identifying subclasses of leukocytes whose phagocytic and killing ability is to be determined, based upon the parameters of forward angle and right angle light scatter.

7. The method as provided in claim 6 wherein the first fluorescent label is tetramethyl rhodamine and the second fluorescent label is fluorescein.

8. The method as provided in claim 6 wherein the target particles are selected from the group consisting of plastic beads having a diameter in the range of about one to two micrometers and bacteria.

9. A method for the simultaneous detection of leukocyte phagocytic and killing ability comprising:
    (a) providing a blood sample containing the leukocytes to be detected;
    (b) providing target particles to be phagocytosed by said leukocytes, said particles having associated therewith a first fluorescent label and a second fluroescent label having an emission spectrum substantially different from said first fluorescent label, said second fluorescent label additionally having a substantially greater photodecomposition sensitivity to reactive oxygen than said first fluorescent label whereby in the presence of said reactive oxygen, said second fluorescent label is substantially less fluorescent;
    (c) incubating said cells with said particles;
    (d) lysing erythrocytes contained in said blood sample;
    (e) detecting those leukocytes whose phagocytic and killing ability is to be determined;
    (f) identifying those cells having phagocytic ability based on their first label fluorescence and discriminating those cells having killing ability and producing reactive oxygen based on their ratio of first label fluorescence to second label fluorescence.

10. The method as provided in claim 9 wherein the target particles are selected from the group consisting of plastic beads having a diameter in the range of about one to two micrometers and bacteria.

11. The method as provided in claim 9 wherein the first or second fluorescent label is substituted with colloidal gold and the identifying step measures the back scattering of light produced by said colloidal gold label.

12. The method as provided in claim 9 wherein the killing ability is determined by measuring the shift in the mean of the red to green fluorescent ratios.

13. The method as provided in claim 12 wherein the target particles are selected from the group consisting of plastic beads having a diameter in the range of about one to two micrometers and bacteria.

* * * * *

UNITED STATES PATENT AND TRADEMARK OFFICE
CERTIFICATE OF CORRECTION

PATENT NO. : 4,581,334

DATED : April 8, 1986

INVENTOR(S) : Stefan J. Kirchanski, Giora Davidovits, Robert A. Hoffman

It is certified that error appears in the above-identified patent and that said Letters Patent is hereby corrected as shown below:

Column 8, line 2, "rohodamine"

should be --rhodamine--.

Signed and Sealed this

Thirteenth Day of January, 1987

*Attest:*

DONALD J. QUIGG

*Attesting Officer*     *Commissioner of Patents and Trademarks*